US011185660B2

(12) United States Patent
Connell, II et al.

(10) Patent No.: US 11,185,660 B2
(45) Date of Patent: *Nov. 30, 2021

(54) AIRBORNE ANXIETY DETECTION AND REMEDIATION

(71) Applicant: INTERNATIONAL BUSINESS MACHINES CORPORATION, Armonk, NY (US)

(72) Inventors: Jonathan H. Connell, II, Cortlandt-Manor, NY (US); Robert G. Farrell, Cornwall, NY (US); Nalini K. Ratha, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 255 days.

This patent is subject to a terminal disclaimer.

(21) Appl. No.: 16/538,051

(22) Filed: Aug. 12, 2019

(65) Prior Publication Data

US 2019/0358429 A1    Nov. 28, 2019

Related U.S. Application Data

(63) Continuation of application No. 15/291,277, filed on Oct. 12, 2016, now Pat. No. 10,420,913.

(51) Int. Cl.
*A61M 21/02* (2006.01)
*A61B 5/16* (2006.01)
(Continued)

(52) U.S. Cl.
CPC .......... *A61M 21/02* (2013.01); *A61B 5/0022* (2013.01); *A61B 5/02438* (2013.01);
(Continued)

(58) Field of Classification Search
CPC ... A61B 5/0022; A61B 5/024; A61B 5/02438; A61B 5/165; A61B 5/681; A61M 21/02;
(Continued)

(56) References Cited

U.S. PATENT DOCUMENTS 5,304,112 A     4/1994   Mrklas et al.
5,807,114 A     9/1998   Hodges et al.
(Continued)

OTHER PUBLICATIONS

List of IBM Patents or Patent Applications Treated as Related; Date Filed: Aug. 12, 2019, 2 pages.
(Continued)

*Primary Examiner* — Christine H Matthews
(74) *Attorney, Agent, or Firm* — Cantor Colburn LLP; Stosch Sabo

(57) ABSTRACT

Embodiments include methods, systems, and computer program products for detection and remediation of anxiety. Aspects include receiving an anxiety indicator. Aspects also include analyzing the anxiety indicator to determine whether an anxiety level exceeds an anxiety threshold. Aspects also include, based upon a determination that the anxiety level exceeds the anxiety threshold, selecting a first sound. Aspects also include outputting the first sound. Aspects also include receiving an anxiety feedback. Aspects also include determining, based upon the anxiety feedback, whether the anxiety level is decreasing.

20 Claims, 5 Drawing Sheets

(51) Int. Cl.
    *A61B 5/00*         (2006.01)
    *A61B 5/024*       (2006.01)
    *A61B 5/0533*     (2021.01)
    *A61M 21/00*      (2006.01)
    *A61B 5/01*         (2006.01)
    *A61B 5/021*       (2006.01)

(52) U.S. Cl.
    CPC ............ *A61B 5/0533* (2013.01); *A61B 5/165* (2013.01); *A61B 5/681* (2013.01); *A61B 5/6893* (2013.01); *A61B 5/746* (2013.01); *A61B 5/01* (2013.01); *A61B 5/021* (2013.01); *A61B 5/024* (2013.01); *A61B 5/02405* (2013.01); *A61M 2021/0027* (2013.01); *A61M 2205/3553* (2013.01); *A61M 2205/3584* (2013.01); *A61M 2205/50* (2013.01); *A61M 2205/502* (2013.01); *A61M 2205/52* (2013.01); *A61M 2230/06* (2013.01); *A61M 2230/30* (2013.01); *A61M 2230/42* (2013.01); *A61M 2230/50* (2013.01)

(58) Field of Classification Search
    CPC .......... A61M 2021/0027; A61M 21/00; A61M 2021/005
    See application file for complete search history.

(56) References Cited

U.S. PATENT DOCUMENTS

| | | |
|---|---|---|
| 10,420,913 B2 * | 9/2019 | Connell, II ............ A61B 5/165 |
| 2003/0166996 A1 | 9/2003 | Kim et al. |
| 2005/0131273 A1 | 6/2005 | Asano et al. |
| 2010/0240945 A1 | 9/2010 | Bikko |
| 2010/0331607 A1 | 12/2010 | Pelgrim et al. |
| 2013/0211277 A1 | 8/2013 | Berg et al. |
| 2016/0267405 A1 | 9/2016 | Reiner |

OTHER PUBLICATIONS

Collingwood, Jane, "The Power of Music to Reduce Stress"; accessed online Sep. 15, 2016, six pages.

Fitzpatrick, Frank, "12 Ways to Reduce Stress with Music"; accessed online Sep. 15, 2016; 5 pages.

Benford, M. Sue et al., "Use of Electrodermal Activity for Assessment of Pain/Stress in Laboratory Animals" accessed Sep. 15, 2016, 15 pages.

Thoma et al., "The Effect of Music on the Human Stress Response," PLOS One, Aug. 2013, vol. 8, e70156., 12 pages.

\* cited by examiner

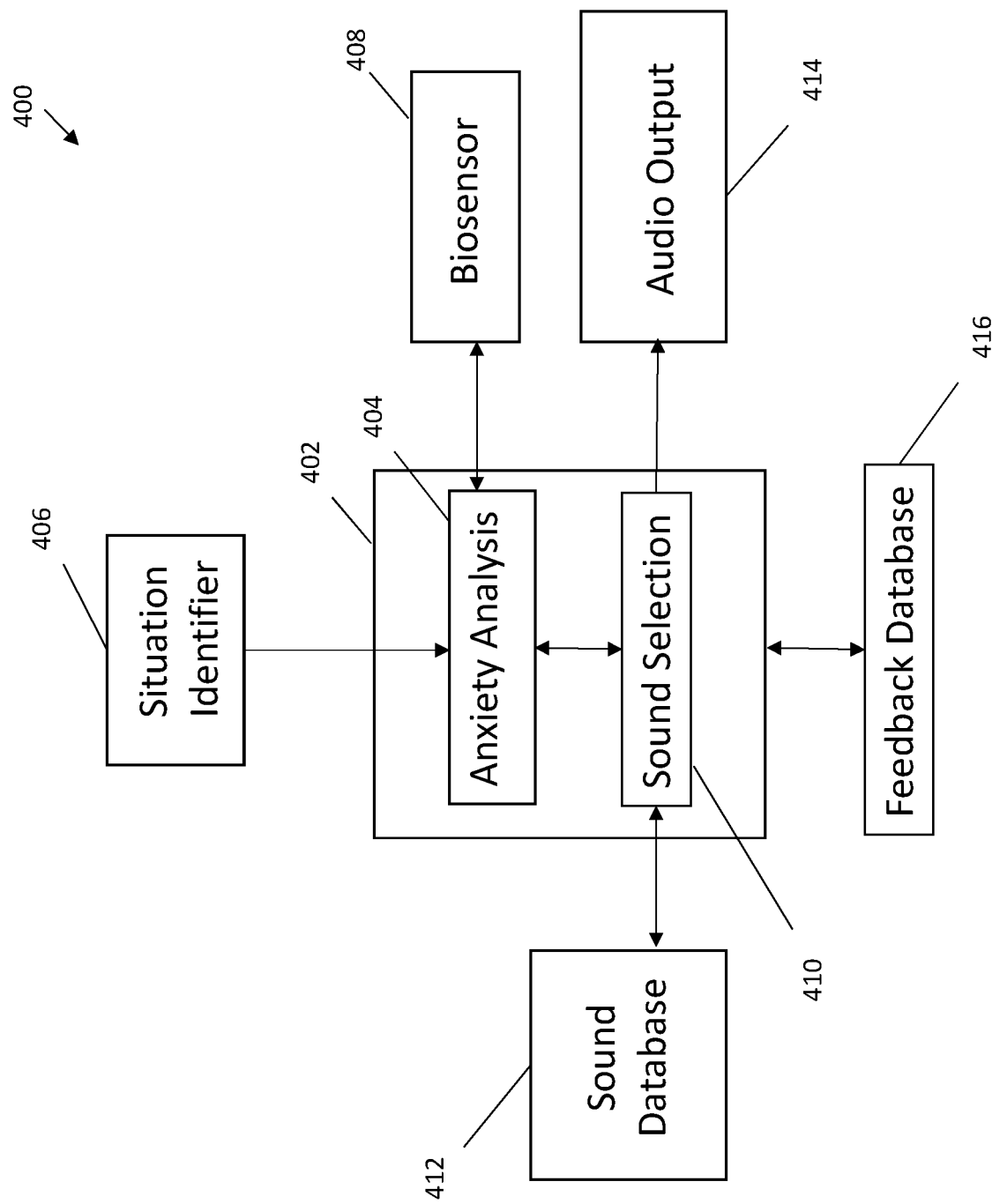

AIRBORNE ANXIETY DETECTION AND REMEDIATION

DOMESTIC PRIORITY

This application is a continuation of U.S. patent application Ser. No. 15/291,277, filed Oct. 12, 2016, the disclosure of which is incorporated by reference herein in its entirety.

BACKGROUND

The present invention relates to detection and remediation of anxiety and, more specifically, to automated methods, systems and computer program products for detection and remediation of anxiety with audible interaction.

People can experience anxiety in a number of situations. For instance, taking tests, visiting a physician, or traveling by air can cause a number of people to become anxious. A variety of sensory, medical, biological, and psychological methods have been associated with reduction of anxiety. For example, meditation has been associated with a decrease in anxiety levels for some people in certain situations. Similarly, certain sounds or fragrances have also been associated with a decrease in anxiety levels for certain people in certain situations. The effectiveness of a method of reducing anxiety can vary based upon the individual in question. In addition, for a given individual, an effective method for reducing anxiety in one situation might not be suitable or might not work for other situations.

SUMMARY

In accordance with one or more embodiments, a computer-implemented method for detection and remediation of anxiety is provided. The method includes receiving, by a processor, an anxiety indicator. The method also includes analyzing the anxiety indicator to determine whether an anxiety level exceeds an anxiety threshold. The method also includes based upon a determination that the anxiety level exceeds the anxiety threshold, selecting, by the processor, a first sound. The method also includes outputting the first sound. The method also includes receiving an anxiety feedback. The method also includes determining, based upon the anxiety feedback, whether the anxiety level is decreasing.

In accordance with another embodiment, a computer program product for detection and remediation of anxiety is provided. The computer program product includes a non-transitory storage medium readable by a processing circuit and storing instructions for execution by the processing circuit for performing a method including receiving an anxiety indicator. The method also includes analyzing the anxiety indicator to determine whether an anxiety level exceeds an anxiety threshold. The method also includes based upon a determination that the anxiety level exceeds the anxiety threshold, selecting a first sound. The method also includes outputting the first sound. The method also includes receiving an anxiety feedback. The method also includes determining, based upon the anxiety feedback, whether the anxiety level is decreasing.

In accordance with a further embodiment, a processing system for detecting and remediating anxiety includes a processor in communication with one or more types of memory. The processor is configured to receive an anxiety indicator. The processor is also configured to analyze the anxiety indicator to determine whether an anxiety level exceeds an anxiety threshold. The processor is also configured to, based upon a determination that the anxiety level exceeds the anxiety threshold, select a first sound. The processor is also configured to output the first sound. The processor is also configured to receive an anxiety feedback. The processor is also configured to determine, based upon the anxiety feedback, whether the anxiety level is decreasing.

BRIEF DESCRIPTION OF THE DRAWINGS

The subject matter of the present invention is particularly pointed out and distinctly claimed in the claims at the conclusion of the specification. The foregoing and other features and advantages of the one or more embodiments described herein are apparent from the following detailed description taken in conjunction with the accompanying drawings in which:

FIG. 5 depicts a diagram illustrating an exemplary system for detecting and remediating anxiety according to one or more embodiments of the present invention.

DETAILED DESCRIPTION

Figure 1:
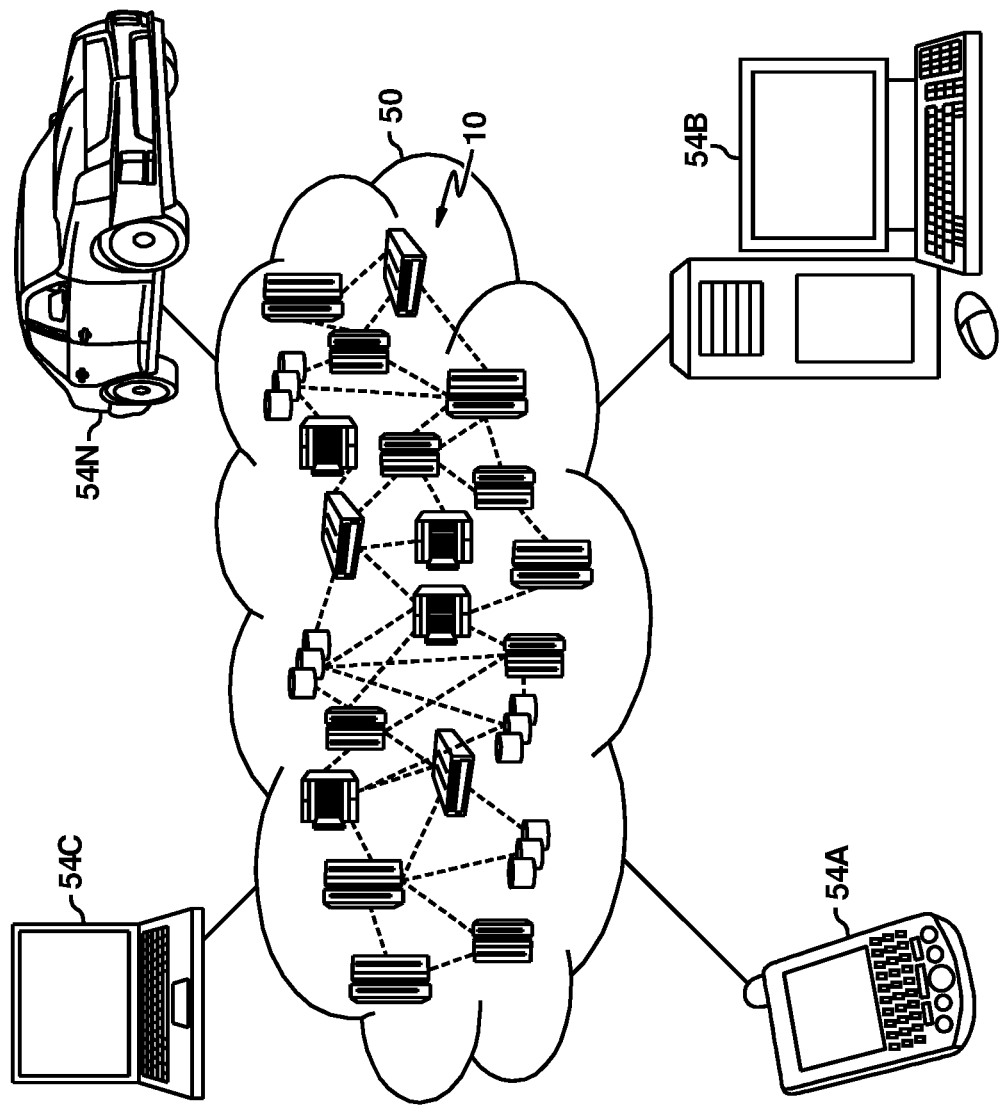
FIG. 1 depicts a cloud computing environment according to an embodiment of the present invention.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 is depicted, according to an embodiment of the present invention. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
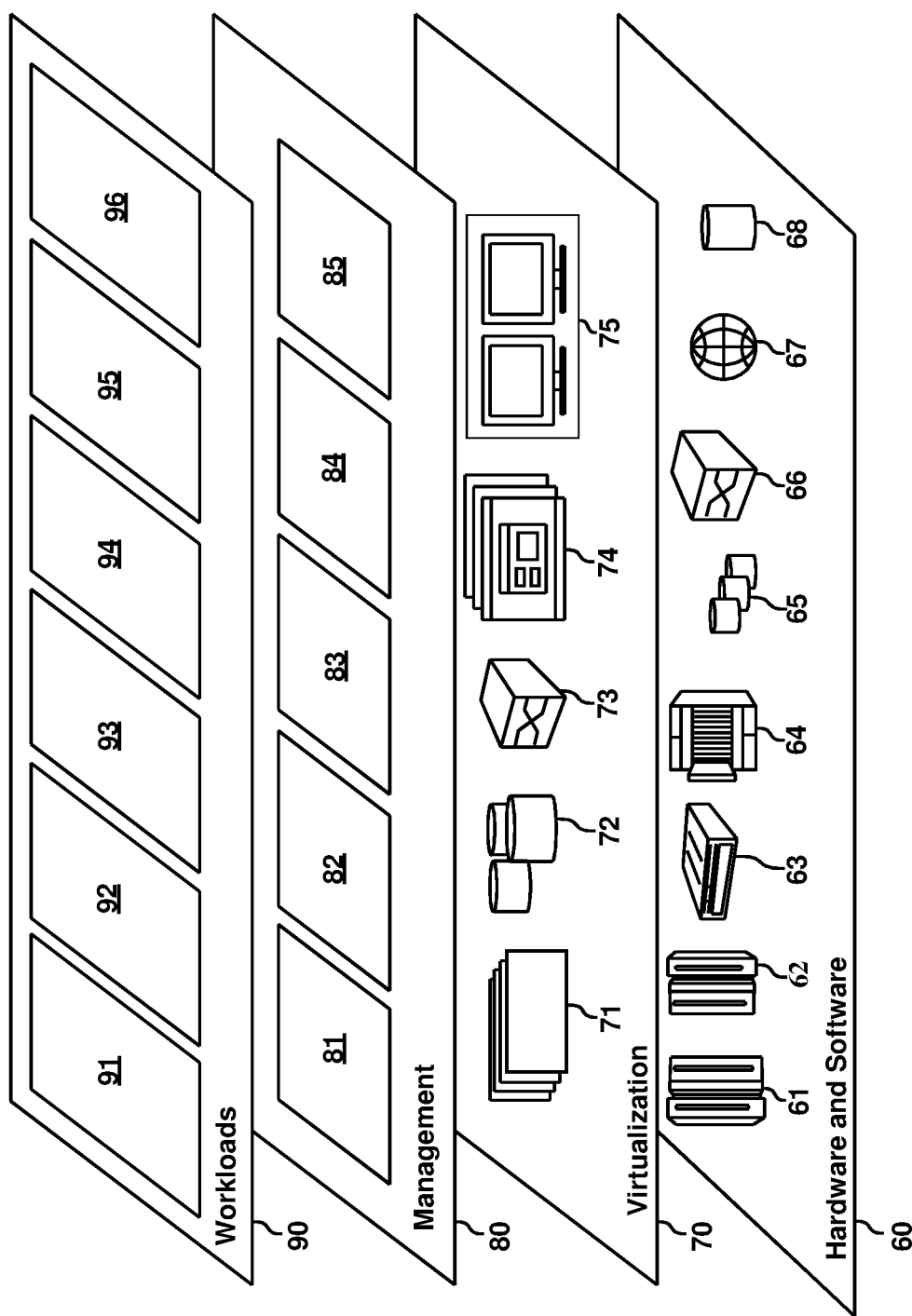
FIG. 2 depicts abstraction model layers according to an embodiment of the present invention.

Referring now to FIG. 2, a set of functional abstraction layers provided by cloud computing environment 50 (FIG. 1) is depicted, according to an embodiment of the present invention. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and detecting and remediating anxiety with audible interaction that provides audible feedback 96.

Figure 3:
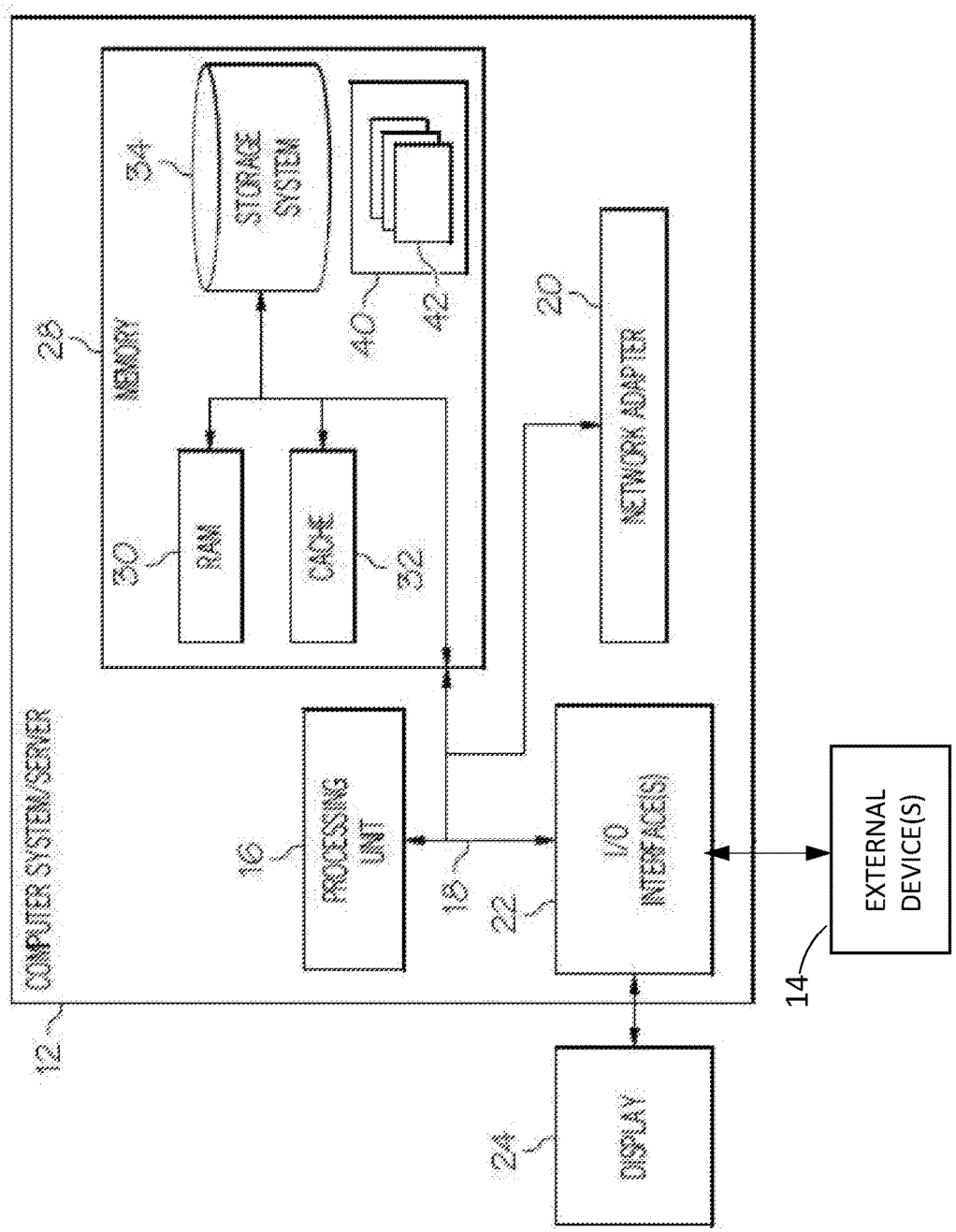
FIG. 3 depicts a computing node according to one or more embodiments of the present invention.

Referring now to FIG. 3, a schematic of a computing node 100 that can be included in a distributed cloud environment or cloud service network is shown according to a non-limiting embodiment of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100, according to one or more embodiments of the present invention, is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of embodiments of the present invention, systems and methodologies for airborne anxiety detection and remediation are provided. People can become anxious in a variety of situations, such as taking tests, seeing a doctor, or traveling by air. Anxiety, particularly high levels of anxiety, can be detrimental to a person's health and performance. Modes of anxiety reduction can include medication-based methods, meditation-based methods, personal psychological comforting, interaction with a comfort object, and other sensory methods including aroma therapy and the use of soothing music.

Embodiments described herein can detect and remediate anxiety. In some embodiments, using mobile wearable devices such as smart watches and bands, input are received and analyzed in order to detect high anxiety levels. For instance, mobile wearable devices can have biological sensors, such as heart rate monitors, blood pressure monitors and the like. An elevated blood pressure level, for example, can indicate an elevated anxiety level. Input from biological sensors, therefore, can be analyzed to determine a user's anxiety level. In addition, situational data, such as GPS information and accelerometer data, can identify or confirm stressful locations or stressful sudden movements, such as an airplane take-off or landing situation. Such situational data can be combined and analyzed to determine an anxiety level. For example, a hospital can be an inherently stressful location for a user. This location information can be combined with other information, such as a user's accelerometer which registers pacing back and forth and a biological sensor indicating an elevated blood pressure. After detection of an elevated anxiety level, embodiments include remediation of anxiety with a computer-implemented automated auditory signal. Embodiments also include personalizing the auditory signal to a user or situation.

Figure 4:
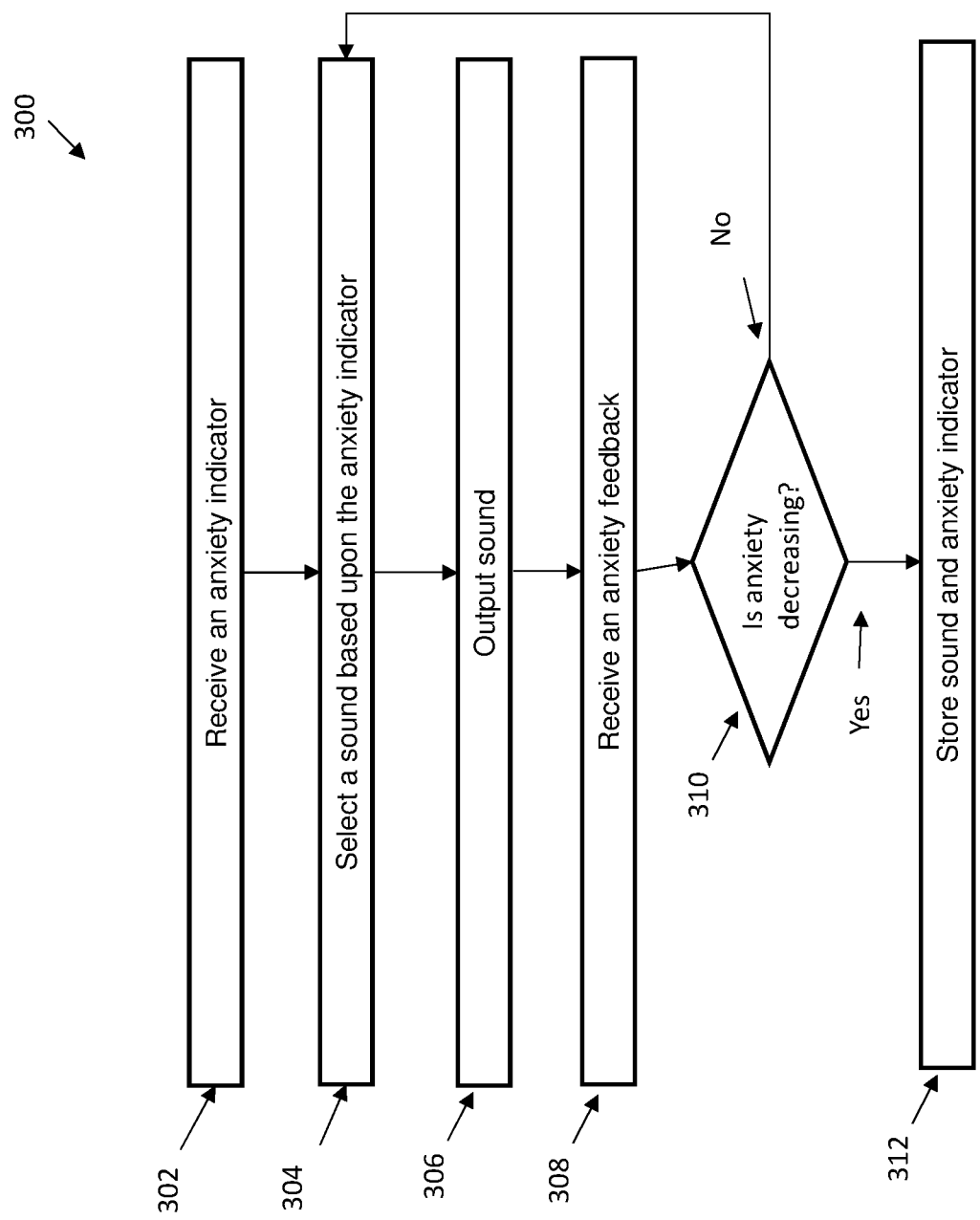
FIG. 4 depicts a flow diagram illustrating a method for detecting and remediating anxiety according to one or more embodiments of the present invention.

Turning now to a more detailed description of one or more embodiments, FIG. 4 depicts a flow chart illustrating an exemplary method 300 for airborne anxiety detection and remediation according to one or more embodiments of the present invention. According to the method 300, an anxiety indicator is received as shown at block 302. The method 300 also includes, as shown at block 304, selecting a sound based upon the anxiety indicator. The method 300 also includes outputting a sound, as shown at block 306. As shown at block 308, the method includes receiving an anxiety feedback. Then, as is shown at decision block 310, the method 300 asks whether anxiety is decreasing. If anxiety is not decreasing, the method returns to block 304 and selects a sound based upon the anxiety indicator. If anxiety is decreasing, the method 300 stores the sound and anxiety indicator, as is shown at block 312. In some embodiments, if anxiety is not decreasing, the method includes storing the sound and anxiety indicator with data reflecting that anxiety did not decrease.

A sound can be output gradually or abruptly. In some embodiments, when a sound is output, the sound gradually increases in volume to a desired level. In some embodiments, when a sound is output the volume is fixed at a desired level and the volume is constant.

In some embodiments, if anxiety has decreased below a desired level, the method includes terminating the sound. Terminating the sound can include an abrupt or gradual termination of a sound. For example, in some embodiments, if anxiety has decreased below a desired level, the sound can gradually or automatically fade such that the volume is slowly reduced over time.

The stored data can be used to inform subsequent sound selections. For example, a determination that country music did not reduce a user's anxiety levels in a doctor's office can be stored. Subsequently, when situational data indicates a user is in a doctor's office, the stored data can be used to select a sound and can cause a genre of music other than country music to be selected to reduce the user's anxiety level.

In some embodiments, if anxiety is not decreasing, a second sound is selected and provided to an output. The second sound can be a different audible signal likely to reduce anxiety in the individual. For example, the second sound can be a different genre of music associated with anxiety reduction, a different song associated with anxiety reduction, a different song selected from the anxious individual's playlist, or a tone associated with anxiety reduction. The likelihood of anxiety reduction can be based upon that individual's history or preferences or other individuals' histories and preferences. The second song can be selected randomly from a database, sequentially from a predetermined list, or in any other manner.

In some embodiments, methods include analyzing an anxiety indicator to determine whether an anxiety level exceeds an anxiety threshold. An anxiety indicator includes a datum or data that informs of an anxious status. In some embodiments, the anxiety indicator includes biological data. Biological data that informs of an anxious status can include heart rate, blood pressure, body temperature, respiration rate, or any other biological or biophysical data that is associated with an anxious state. For example, when an individual experiences anxiety, that individual can experience an increased heart rate, increased blood pressure, and increased respiration rate. Biological data can be collected through the use of biosensors.

Biological data can be analyzed, for example, by determining or obtaining a baseline reading from a biosensor and then comparing biological data, such as real-time biological data, to the baseline reading. In some embodiments, norms or standardized values can be provided prior to or in addition to providing a baseline. After a baseline reading or measurement, in some embodiments a system measures anxiety indicators and determines whether significant deviations are present.

In some embodiments, based upon a determination that the anxiety level exceeds the anxiety threshold, a first sound is selected. In some embodiments, prior to selection of a sound, an anxiety signal is provided to a user. The anxiety signal can include, for example, a notification to a user that the anxiety level is high, an instruction to the user to calm down, or a notification or query to play an anxiety-reducing sound. For example, if a user is determined to be anxious, a method can notify the user that a high anxiety level was detected and then notify the user that a song will be played. In some embodiments, methods include querying the user to determine whether the user will allow a sound output prior to outputting a sound.

Embodiments include selecting a sound. A sound can be a song, a tone, or a series of tones and can be selected from a pre-selected list of songs or sounds that have been calibrated to reduce anxiety. In some embodiments, the volume, timbre, modulation, class, genus, or other aspects of the sound can be modified to improve anxiety reduction. Sounds can be selected from a user's music database or from an external database. For example, music or sounds can be downloaded to conform to a specific situation. Music can have associated metadata that can be used for filtering, such as genre information. In some embodiments, music is selected based upon metadata. In some embodiments, music is selected based upon user preferences.

Sound can be output to any device that provides an audible signal to the user. For example, sound can be output to a user's headphones or blue tooth device, speakers of a smartphone or smart watch, speakers to a laptop or tablet, or to speakers of an automobile or home entertainment system. In some embodiments, the volume of the sound can be adjusted by a user. In some embodiments, the volume of the sound can be automatically adjusted based upon situational information. For example, if it is determined that a user is experiencing anxiety in a doctor's office, the volume can be lowered to reduce discomfort to other patients.

In some embodiments, systems include a display. The display can include an anxiety level, for example. In some embodiments, display can include music selections. For example, an audio output can be used in combination with a display to show a user the level of anxiety and allow a user to press a button to play a selected sound. The playing of music can become the feedback indicating the user is indeed anxious and the system can then continue to monitor the anxiety levels until they fall below a threshold.

In some embodiments, an anxiety level is predicted. For example, situational data can be predetermined from a calendar, GPS data, or accelerometer data. For example, a method can include determining that a person is at an airport and, therefore, likely to experience anxiety due to air travel in the near future. In some embodiments, a sound can be output based upon a predicted high anxiety level. In some embodiments, methods include calculating a probability of an anxiety level above a threshold and outputting a sound based upon the predicted high anxiety level. In some embodiments, a sound can be output as a preventative measure to preclude high anxiety. A probability of high anxiety can be predicted based upon situational and/or biophysical data. In some embodiments, a probability of high anxiety is calculated based upon data from a biosensor. In some embodiments, systems include a classifier that calculates a high probability context based upon sensor data and/or situational data.

Anxiety feedback includes data that can be used to determine an anxiety level, including real-time data. In some embodiments, the anxiety feedback includes real-time biological or situational data.

In some embodiments, a user can control the auditory output. For example, a user can stop the music at any time or fade music or a sound. In some embodiments, methods include changing a music selection or music volume responsive to a user request.

FIG. 5 illustrates an exemplary system 400 for airborne anxiety detection and remediation according to one or more embodiments of the present invention. The exemplary system 400 includes a processing system 402. The processing system includes an anxiety analysis component 404. The anxiety analysis component 404 receives input from external sources. In some embodiments, as is illustrated, the anxiety analysis component receives input from a biosensor 408. The anxiety analysis component 404 can also receive input from a situation identifier 406. The anxiety analysis component 404 is in communication with a sound selection component 410. The sound selection component 410 receives input from a sound database 412. The sound selection component 410 is connected to an audio output 414. Audio output 414 includes any audio system capable of providing music within ear shot of an individual. For example, audio output can include headphones, speakers in smart devices, automotive output systems, and the like. The processing system 402 of the exemplary system 400 is in communication with a feedback database 416. Biosensor 408 includes any device that obtains or measures a biological or biophysical output. For example, biosensors 408 include heart rate monitors, blood pressure monitors, pulse oximeters, thermometers, respiration monitors, electro dermal activity (EDA) sensors, and manual user input informing of a biological or biophysical state. Situation identifier 406 includes data that provides situational information, such as GPS or other location information, calendar data, or accelerometer data.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for detection and remediation of anxiety, the method comprising:
   receiving, by a processor, a biological sensor input from a mobile wearable device worn by a user;
   receiving, by the processor, a situational data input comprising a GPS location of the user;
   determining that the GPS location is associated with an increased anxiety level for the user;
   determining whether a current anxiety level exceeds an anxiety threshold based at least in part upon the biological sensor input and the situational data input;
   selecting, by the processor, a first sound based upon a determination that the current anxiety level exceeds the anxiety threshold; and
   outputting the first sound via a speaker.

2. The computer-implemented method of claim 1, wherein the first sound comprises a tone calibrated to reduce anxiety.

3. The computer-implemented method of claim 1 further comprising adjusting, automatically, a volume of the first sound based upon the situational data input.

4. The computer-implemented method of claim 1 further comprising:
   receiving a second biological sensor input from the mobile wearable device; and
   determining, based upon the biological sensor input and the second biological sensor input, whether the current anxiety level is decreasing.

5. The computer-implemented method of claim 4 further comprising selecting a second sound and outputting the second sound based upon a determination that the current anxiety level is not decreasing.

6. The computer-implemented method of claim 4 further comprising, based upon a determination that the current anxiety level is decreasing, storing feedback data comprising the first sound, the biological sensor input, and the situational data input.

7. The computer-implemented method of claim 1, wherein the biological sensor input comprises data selected from the group consisting of a heart rate, a blood pressure, a body temperature, and a respiration rate.

8. The computer-implemented method of claim 1, wherein the situational data input further comprises accelerometer data.

9. The computer-implemented method of claim 1, wherein the selection of the first sound is personalized for the user.

10. The computer-implemented method of claim 4, wherein the second biological sensor input comprises user feedback.

11. A computer program product for detection and remediation of anxiety, the computer program product comprising a non-transitory computer readable storage medium readable by a processing circuit and storing program instructions for execution by the processing circuit for performing a method comprising:
   receiving a biological sensor input from a mobile wearable device worn by a user;
   receiving a situational data input comprising a GPS location of the user;
   determining that the GPS location is associated with an increased anxiety level for the user;
   determining whether a current anxiety level exceeds an anxiety threshold based at least in part upon the biological sensor input and the situational data input;
   selecting a first sound based upon a determination that the current anxiety level exceeds the anxiety threshold; and
   outputting the first sound via a speaker.

12. The computer program product of claim 11, wherein the first sound comprises a tone calibrated to reduce anxiety.

13. The computer program product of claim 11, the method further comprising adjusting, automatically, a volume of the first sound based upon the situational data input.

14. The computer program product of claim 11, the method further comprising:
   receiving a second biological sensor input from the mobile wearable device; and
   determining, based upon the biological sensor input and the second biological sensor input, whether the current anxiety level is decreasing.

15. The computer program product of claim 11, the method further comprising selecting a second sound and outputting the second sound based upon a determination that the current anxiety level is not decreasing.

16. A processing system for detection and remediation of anxiety, the system comprising a processor in communication with one or more types of memory, the processor configured to:
   receive a biological sensor input from a mobile wearable device worn by a user;
   receive a situational data input comprising a GPS location of the user;
   determine that the GPS location is associated with an increased anxiety level for the user;
   determine whether a current anxiety level exceeds an anxiety threshold based at least in part upon the biological sensor input and the situational data input;
   select a first sound based upon a determination that the current anxiety level exceeds the anxiety threshold; and
   output the first sound via a speaker.

17. The processing system of claim 16, wherein the first sound comprises a tone calibrated to reduce anxiety.

18. The processing system of claim 16, wherein the processor is further configured to, adjust, automatically, a volume of the first sound based upon the situational data input.

19. The processing system of claim 16, wherein the processor is further configured to:
   receive a second biological sensor input from the mobile wearable device; and
   determine, based upon the biological sensor input and the second biological sensor input, whether the current anxiety level is decreasing.

20. The processing system of claim 19, wherein the processor is further configured to select a second sound and output the second sound based upon a determination that the current anxiety level is not decreasing.

* * * * *